US00PP29936P2

(12) United States Plant Patent
Cain

(10) Patent No.: US PP29,936 P2
(45) Date of Patent: Dec. 4, 2018

(54) GRAPEVINE NAMED 'IFG THIRTY-ONE'

(50) Latin Name: ***Vitis interspecific* hybrid**
Varietal Denomination: IFG Thirty-one

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/732,551

(22) Filed: Nov. 28, 2017

(51) Int. Cl.
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para

(57) ABSTRACT

This invention is a new and distinct grapevine variety denominated 'IFG Thirty-one'. The new grapevine 'IFG Thirty-one' is characterized by producing small seedless, purple-black berries having a narrow ellipsoid shape with a unique strong fruity labrusca flavor reminiscent of artificial grape flavor. Fruits normally ripen early to mid-season about late July to early August near Delano Calif.

1 Drawing Sheet

Latin name of the genus and species claimed: *Vitis interspecific* hybrid.

Variety denomination: 'IFG Thirty-one'.

BACKGROUND OF THE INVENTION

The new and distinct grapevine described and claimed herein originated from a hand pollinated cross of the IFG 01124-032-156, an unnamed seedling selection from the IFG breeding program, and the interspecific variety Arkansas 2798 hybridized in May 2006. The abortive seed traces were subsequently embryo cultured and the resulting population of 5 plants was planted in the field in April 2007. The present variety of grapevine was selected as a single plant in July 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Thirty-one' is characterized by producing small purple-black berries having a narrow ellipsoid shape with a unique strong fruity labrusca flavor reminiscent of artificial grape flavor. Fruits normally ripen early to mid-season about late July to early August near Delano Calif. Fruits have medium firm texture, and berries can crack at the tip when fully ripe. Attachment of the berry to the pedicel is somewhat weak. Vines are moderately productive and can be pruned to short spurs. The new grapevine differs from its female parent the IFG 01124-032-156 by having rounder berry shape and by having a very strong fruity labrusca type flavor as opposed to a neutral flavor. 'IFG Thirty-one' can be distinguished from its pollen parent, A2798, by its purple-black color as opposed to black color, by having smaller berry and cluster size.

The interspecific nature of the vine is very evident. Vines are very vigorous with a more erect-horizontal growth habit and large leaves as compared to typical seedless grapes of the *Vitis vinifera* species.

Grape breeders have used several native American grape species to improve hardiness, disease and insect resistance as well as incorporate aromatic flavors into the *vinifera* species. Previously introduced interspecific varieties have had very limited commercial success due to small fruit size, large seed traces, slipskin texture or lack of firmness. The new grapevine variety is being introduced because of its unique labrusca flavor combined with seedlessness, and good adhesion of skin.

BRIEF DESCRIPTION OF THE DRAWING

The accompanying photographic drawing in FIG. 1 illustrates in full color 'IFG Thirty-one'. The photograph was taken outdoors with indirect lighting. The colors are as nearly true as is reasonably possible in a color representation of this type. The left side of the drawing has a mature leaf. A mature fruit cluster is represented in the center of the drawing along with a typical berry in cross section. A young shoot tip with tendrils and young leaves can be seen on th right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the UPOV International Union for the Protection of New Varieties of Plants publication 'Grapevine *Vitis* L. Guidelines' (TG/50/9) (Apr. 9, 2008), (www.upov.int/edocs/tgdocs/en/tg050.pdf).

The descriptive matter which follows pertains to 'IFG Thirty-one' plants grown in the vicinity of Delano, Kern County, Calif. during 2012, and is believed to apply to plants of the variety grown under similar conditions of soil and climate elsewhere:

VINE

General:
- *Vigor*.—Vigorous.
- *Density of foliage*.—Dense.
- *Productivity*.—Moderately productive, producing about 17.5 to 26.2 kg of fruit per vine.
- *Root stock*.—Own root.
- *Training method*.—Typically spur pruned leaving 2 bud spurs.

Trunk:
- *Trunk diameter of* 4-*year-old vines at* 30 *cm above the soil line*.—About 4.9 cm.
- *Shape*.—Stocky to medium.
- *Straps*.—Short — split.
- *Surface texture*.—Shaggy.
- *Inner bark color*.—Greyed-orange: 165A.

SHOOTS

Young shoot:
- *Form of tip*.—Wide opened.
- *Distribution of anthocyanin coloration of tip*.—Absent.
- *Intensity of anthocyanin coloration of tip*.—Very weak.
- *Density of prostrate hairs on tip*.—Sparse to medium.
- *Density of erect hairs on tip*.—Absent.
- *Color*.—The following colors were observed: Yellow-green: 144A and 144B, and 146A.

Woody shoot (mature canes):
- *Internode length*.—Medium: About 7.1 cm.
- *Width at node*.—About 0.7 cm.
- *Cross section*.—Circular.
- *Surface*.—Striate.
- *Main color*.—The following colors were observed: Greyed-orange: 164A and 164B and 164C and 164D.
- *Density of erect hairs on nodes*.—Sparse.
- *Density of erect hairs on internodes*.—None.
- *Axillary shoot length at full bloom*.—Medium: Approximately 14.0 cm.

Flowering shoot:
- *Vigor during flowering*.—Very strong.
- *Attitude during flowering on shoots not tied*.—Semi-erect.
- *Color*.—Dorsal side of internodes — Yellow-green: 146C, with Red-purple stripes: 59B.
- *Color*.—Ventral side of internodes — Yellow-green: 146C.
- *Color*.—Dorsal side of nodes — Yellow-green: 146C, and Yellow-green: 146C with Red-purple stripes: 59B.
- *Color*.—Ventral side of nodes — Yellow-green: 146C.
- *Density of prostrate hairs on nodes*.—Very sparse.
- *Density of erect hairs on nodes*.—Very sparse.
- *Density of prostrate hairs on internode*.—Very sparse.
- *Density of erect hairs on internode*.—None.
- *Anthocyanin coloration of buds*.—Absent.

Tendrils:
- *Distribution on the shoot* (*at full flowering*).—Discontinuous.
- *Length of tendril*.—Medium: About 17.7 cm.
- *Thickness of tendril* 2 *cm from base*.—About 1.5 mm.
- *Color*.—The following colors were observed: Yellow-green: N144A and 144A.
- *Form*.—Bifurcated and trifurcated.
- *Number of consecutive tendrils*.—2.

LEAVES

Young leaves:
- *Color of upper surface of first four distal unfolded leaves*.—Yellow-green: 146C.
- *Average intensity of anthocyanin coloration of six distal leaves prior to flowering*.—Weak.
- *Density of prostrate hairs between veins* (*lower surface*).—Absent.
- *Density of prostrate hairs on veins* (*lower surface*).—Sparse.
- *Density of erect hairs between veins* (*lower surface*).—Absent.
- *Density of erect hairs on veins* (*lower surface*).—Medium to dense.

Mature leaves (opposite first cluster):
- *Average length*.—About 16.7 cm.
- *Average width*.—About 17.9 cm.
- *Mature leaf size*.—Medium.
- *Shape of blade*.—Wedge-shaped.
- *Number of lobes*.—5.
- *Blade venation*.—Palmate.
- *Anthocyanin coloration of main veins on upper side of blade*.—Medium.
- *Mature leaf profile*.—Flat.
- *Blistering surface of blade upper surface*.—Very weak.
- *Leaf blade tip*.—In the plane of the leaf.
- *Undulation of margin*.—Slight.
- *Undulation of blade between main and lateral veins*.—Only near petiole.
- *Shape of teeth*.—Mixture of both sides straight and both sides convex.
- *Length of teeth*.—Short.
- *Ratio length/width of teeth*.—Small.
- *Shape of upper lateral sinuses*.—Lobes slightly overlapping.
- *Depth of upper lateral sinuses*.—Shallow to medium.
- *General shape petiole sinus*.—Half open.
- *Shape of base of upper leaf sinuses*.—U-shaped.
- *Tooth at petiole sinus*.—Absent.
- *Density of prostrate hairs between veins on lower surface of blade*.—Absent.
- *Density of erect hairs between veins on lower surface of blade*.—Absent.
- *Density of prostrate hairs on main veins on lower surface of blade*.—None.
- *Density of erect hairs on main veins on lower surface of blade*.—Medium.
- *Density of prostrate hairs on main veins on upper surface of blade*.—Very sparse.
- *Density of erect hairs on main veins on upper surface of blade*.—Sparse to medium.
- *Autumn coloration of leaves*.—Leaves can be a single color or a combination of colors, in a mottled pattern or on the edges of the leaves. The following colors were observed: Yellow-orange: 14C and 14D, and Orange-red: N34A and N34B and N34C, and Greyed-purple: 187A and 187B.

Upper surface:

*Color*.—The following colors were observed: Green: 137A and 137B, and Yellow-green: 147A.

*Anthocyanin coloration of main veins*.—Weak to medium.

*Surface appearance*.—Dull.

*Blistering surface of blade*.—Very weak.

Lower surface:

*Color*.—The following colors were observed: Green: 138A and 137C.

*Anthocyanin coloration of main veins* (*lower surface*).—Medium.

*Glossiness*.—Weak.

*Surface texture*.—Smooth.

*Surface appearance*.—Semi-glossy to dull.

Petiole:

*Length*.—About 16.2 cm.

*Diameter of petiole* 2 *cm from blade*.—About 2.7 mm.

*Petiole color*.—The following colors were observed: Yellow-green: 145C and Greyed-red: 182C.

*Length of petiole compared to middle vein*.—Equal.

*Density of prostrate hairs on petiole*.—None.

*Density of erect hairs on petiole*.—Sparse.

Buds:

*Bud fruitfulness*.—Basal: Mostly fruitful.

*Position of first fruitful shoot on previous season cane*.—$1^{st}$ to $2^{nd}$ node.

*Dormant bud length*.—About 6.0 mm.

*Dormant bud width in the proximal/distal plane*.—About 6.3 mm.

*Dormant bud color*.—Greyed-orange: 165B.

*Time of bud burst*.—Midseason: about May 17, 2012.

FLOWERS

General:

*Flower sex*.—Hermaphrodite.

*Length of first inflorescence*.—Short to medium: About 14.9 cm long by 5.3 cm wide.

*Position of first flowering and fruiting node*.—$3^{rd}$ node (current season growth).

*Number of inflorescence per flowering shoot*.—2.1 to 3.

*Time of bloom*.—Midseason as compared with similar varieties in the growing area of Delano, Calif.

*Date of full bloom*.—About May 15, 2012.

FRUIT

General:

*Ripening period*.—Early to mid season: Approximately Aug. 9, 2012.

*Use*.—Fresh market.

*Keeping quality*.—Moderate, can be prone to shatter during handling and storage at 0° C. and high RH.

*Resistance to*.—Insects: Average typical of *Vitis vinifera* species. Diseases: Average typical of *Vitis vinifera* species.

*Refractometer test*.—Soluble solids: about 19.0 Brix.

*Brix/acid*.—About 30.6.

*Titratable acidity*.—About 0.62.

*Juice ph*.—About 3.3.

*Juice color*.—Greyed-brown: 199D.

Cluster:

*Mature cluster length* (*peduncle excluded*).—About 24.2 cm.

*Mature cluster width*.—About 13.7 cm.

*Mature cluster weight*.—About 582 g.

*Bunch density*.—Medium.

*Number of berries*.—About 130.

*Form*.—Conical.

Peduncle:

*Lignification of peduncle*.—Weak.

*Length of peduncle*.—Short: Approximately 2.3 cm.

Berry:

*Uniformity of size*.—Uniform.

*Single berry weight*.—About 4.9 g natural: to about 7.1 g when treated with gibberellic acid.

*Shape*.—Narrow ellipsoid.

*Seeds*.—Absent.

*Cross section*.—Circular.

*Berry dimensions*.—Longitudinal axis: about 2.3 cm horizontal axis: about 1.8 cm.

*Berry firmness*.—Medium.

*Particular flavor*.—Labrusca.

*Bloom* (*cuticular wax*).—Medium.

*Berry separation from pedicel*.—Easy.

*Skin color* (*without bloom*).—Greyed-purple: 187A and 187B.

Skin:

*Thickness*.—Medium.

*Skin toughness*.—Not notable when chewing.

*Reticulation*.—Absent.

*Tenacity*.—Tenacious to flesh.

What is claimed:

1. A new and distinct variety of grapevine as herein illustrated and described.

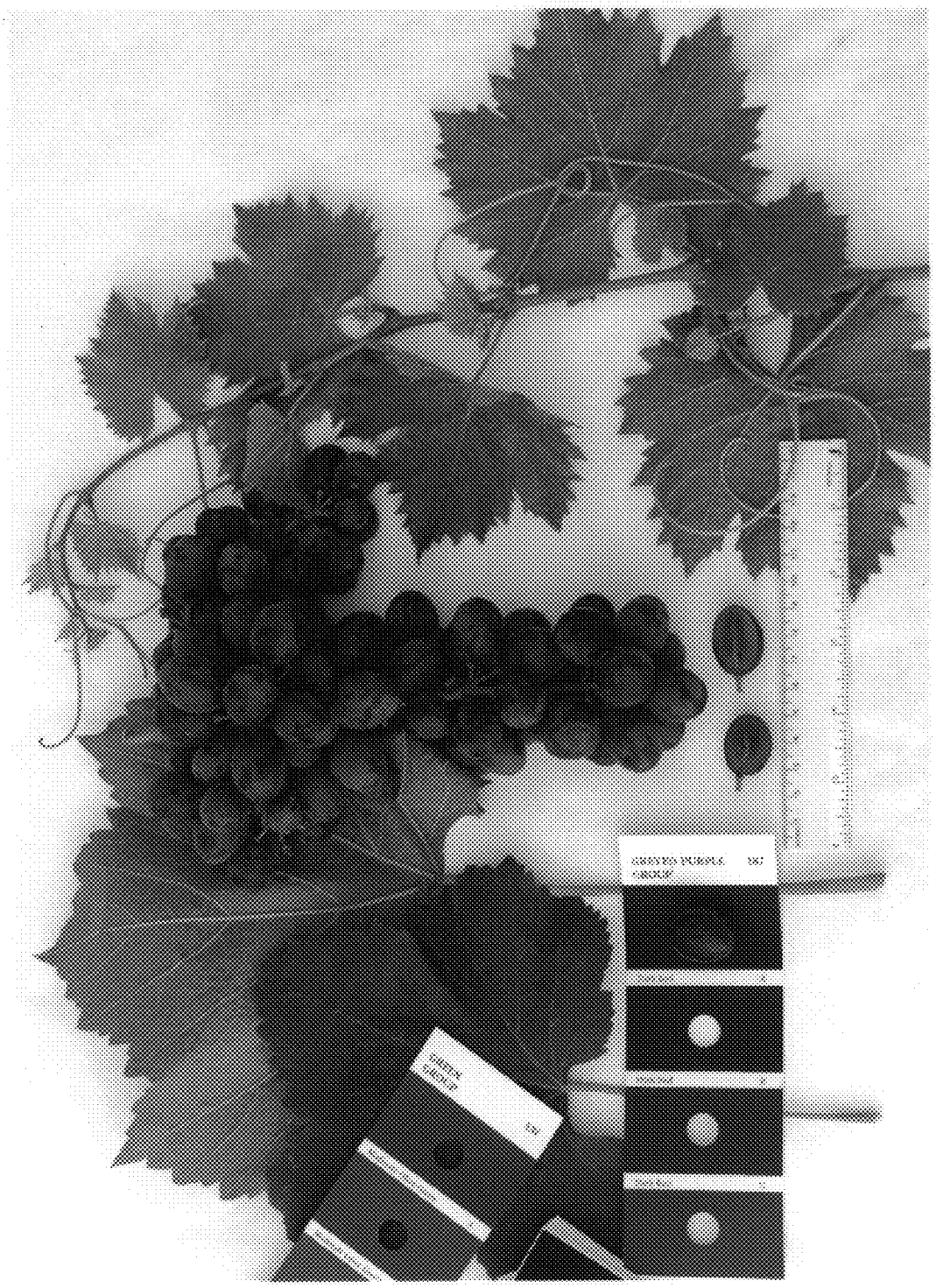

* * * * *